United States Patent [19]

Regier

[11] 4,216,194

[45] Aug. 5, 1980

[54] METHOD OF PRODUCING METHANE AND CARBON

[75] Inventor: Robert B. Regier, Bartlesville, Okla.

[73] Assignee: Phillips Petroleum Company, Bartlesville, Okla.

[21] Appl. No.: 629,432

[22] Filed: Nov. 6, 1975

Related U.S. Application Data

[63] Continuation-in-part of Ser. No. 459,622, Apr. 10, 1974, abandoned.

[51] Int. Cl.$^2$ ............................ C07C 1/04; C09C 1/48
[52] U.S. Cl. ............................ 423/459; 260/449.6 M; 260/449 M
[58] Field of Search ................... 260/449 M, 449.6 M; 48/197; 423/459, 444, 450, 453, 458

[56] References Cited

U.S. PATENT DOCUMENTS

| | | | |
|---|---|---|---|
| 3,453,146 | 7/1969 | Bawa et al. | 48/214 A |
| 3,488,226 | 1/1970 | Baker | 252/466 J |
| 3,511,624 | 5/1970 | Humphries et al. | 48/197 |
| 3,600,145 | 8/1971 | Johnson et al. | 260/449.6 M |
| 3,619,144 | 11/1971 | Bawa et al. | 252/373 |
| 3,625,665 | 12/1971 | Thompson | 260/449 M |
| 3,901,667 | 8/1975 | Herrmann | 48/197 |
| 3,979,332 | 9/1976 | Kiovsky et al. | 260/449 M |

OTHER PUBLICATIONS

Beck et al., Alien Property Custodian, Ser. No. 292,742.

*Primary Examiner*—Howard T. Mars

[57] ABSTRACT

Methane and/or carbon are produced when carbon monoxide and hydrogen are passed through a molten salt bath containing suspended therein a finely divided material capable of catalyzing the conversion of carbon monoxide and hydrogen to carbon and/or methane containing gases.

29 Claims, No Drawings

METHOD OF PRODUCING METHANE AND CARBON

This is a continuation-in-part of application Ser. No. 459,622, filed Apr. 10, 1974, now abandoned.

This invention relates to the production of carbon and to the production of a gas containing methane. In one of its aspects the invention relates to a process for producing a gas rich in methane by conversion of carbon monoxide and hydrogen in the presence of a nickel catalyst.

In another aspect this invention relates to the production of carbon from carbon monoxide and hydrogen.

In one of its concepts the invention provides a low temperature catalytic production of carbon black which comprises passing carbon monoxide and hydrogen through a molten salt containing a finely divided and dispersed catalyst, the mole ratio of hydrogen to carbon monoxide being one which favors the production of carbon black and being below about 3.2. In another of its concepts the invention provides for the production of carbon black as herein described utilizing a salt mixture consisting essentially of lithium, sodium, and potassium carbonates in proportions forming a eutectic having a melting temperature of approximately 397° C., permitting the formation of carbon black at a temperature well below the decomposition temperature of any of the salts. In a still further concept of the invention the gaseous phase obtained from the molten salt, upon separation of the carbon black, is passed into a methanation operation thus to obtain a gas which has value for heating and other purposes.

In another of its concepts the invention provides a process for producing a gas rich in methane from carbon monoxide and hydrogen by a methanation reaction conducted in a molten salt bath in which there is suspended a methanation catalyst. In another of its concepts the invention provides such a process wherein a nickel catalyst is suspended in the salt bath. In a further concept the invention provides such a process wherein the catalyst is suspended in a molten ternary eutectic of lithium, sodium and potassium carbonates having a minimum temperature when liquid or molten of about 400° C. In a further concept still the invention provides a two-step process wherein in the first step a methane-containing gas is produced from carbon monoxide and hydrogen, as earlier set forth and later more fully described herein, following which the effluent from the first step is passed into contact with a second catalytic methanation catalyst-containing mass.

I have found that passing a mixture of carbon monoxide and hydrogen through a molten alkali-metal carbonate bath containing suspended iron, cobalt or nickel powder can produce a carbon black having properties rendering it useful in tire production, electrodes, etc. The carbon black which can be obtained, as further described herein, is found to be superior for rubber reinforcing than that which can be obtained in a highly mobile liquid over a finely divided solid catalyst. Hydrogen/carbon monoxide ratio should be below about 3.2:1 and preferably less than the stoichiometric ratio of 3:1 required for methanation of carbon monoxide. I now believe that a portion of the carbon monoxide disproportionates to form carbon black and carbon dioxide and that a portion reacts with the hydrogen to form methane and water. Secondary reactions are also possible depending upon the temperatures and pressures. For example, carbon monoxide can react with the water to form carbon dioxide and hydrogen. The by-product gases can be passed over a second methanation catalyst such as nickel supported on calcium aluminate to finish methanating residual carbon monoxide that may be present. Following this step the carbon dioxide is removed from the effluent by passing it through an absorber containing triethanolamine or the like. The effluent gas which is mostly methane can be used for heating purposes or stored or utilized for other purposes.

I have now also conceived a process which permits catalytic conversion of carbon monoxide and hydrogen to a methane rich gas in which the catalyst is suspended or contained in a molten salt bath. The methanation reaction is extremely exothermic. It is difficult to control the temperature adequately employing conventional means. The molten salt bath serves as a convenient heat transfer means and to regulate the temperature within desirable limits. Additional to the methane contained therein the product resulting from the methanation also will contain hydrogen and some or small amounts of paraffins containing from 2 to about 4 carbon atoms per molecule, as well as carbon oxides. Whenever carbon monoxide content of the reaction effluent is not considered sufficiently reduced, as when the conversion in the melt reactor is too low, it can be further reduced by passing, according to the invention, the effluent over a second catalytic bed containing a conventional methanation catalyst such as nickel supported on calcium aluminate. In this manner, the methane content is substantially increased and the hydrogen and carbon dioxide contents are substantially reduced. At this stage of the operation, however, the initial difficulty to control methanation reaction has been accomplished and the problem of control no longer exists and therefore is not extant in the second step.

There will be formed unavoidably some water owing to the reactions taking place including the reaction of carbon dioxide and hydrogen. The effluent gases preferably are cooled to condense out most of the water. Carbon dioxide content can be reduced to about 1% or less by employing known processes as used by the natural gas industry, that is, carbon dioxide can be removed by using a triethanolamine, hot carbonate solution or by some other process.

The final product thus obtained is suitable for use as a substitute for natural gas. It can be admixed with natural gas to form a blend satisfactory for heating purposes.

It is an object of this invention to produce a methane-containing gas. It is another object of this invention to produce methane from carbon monoxide and hydrogen. It is a further object of this invention to provide a temperature control for the methanation reaction of carbon monoxide and hydrogen as in the presence of a catalyst. It is still a further object of the invention to produce a gas rich in methane from a mixture of carbon monoxide and hydrogen, in controlled manner and in the presence of a catalyst.

Another object of this invention is to produce a form of carbon black. Still another object of the invention is to produce a carbon black suitable for reinforcing rubber, building electrodes, and other purposes. A still further object of the invention is to produce a carbon black at a low temperature compared with that normally used in the production of carbon blacks. A still further object of the invention is to provide a novel process for the production of carbon black employing a catalyst.

Other aspects, concepts, objects and the several advantages of the invention are apparent from a study of this disclosure and the claims.

According to the present invention carbon black is produced by passing a mixture of hydrogen and carbon monoxide through a molten salt in which there is suspended a finely divided material capable of acting at a relatively low temperature as a catalyst for the decomposition of the carbon monoxide to form carbon and some gases.

Also according to the present invention, there is provided a process for the production of methane from carbon monoxide and hydrogen which comprises passing carbon monoxide and hydrogen is desired ratio into a molten bath maintained at a desired temperature, the molten bath containing a suitable catalyst.

Also according to this invention there is provided a process for producing carbon and/or methane containing gas by passing carbon monoxide and hydrogen through a molten salt bath containing a suitable catalyst.

The present invention makes use of a molten salt. The now preferred salt bath is one consisting of alkali metal carbonates. The molten alkali metal carbonate bath now preferred consists of the ternary eutectic of lithium, sodium and potassium carbonates which has the following composition:

|  | Mole % | Weight % |
| --- | --- | --- |
| $Li_2CO_3$ | 43.5 | 32.1 |
| $Na_2CO_3$ | 31.5 | 33.4 |
| $K_2CO_3$ | 25.0 | 34.5 |

The melting point of the mixture of 746.6° F. (397° C.). Hence the minimum temperature used in the process of this invention can be fixed at a somewhat higher temperature, say 399° C. or higher up to about 804° C.

The mixture when molten lends itself well to the methanation reaction, the temperature of which is sought to be controlled, by controlling the salt temperature, within a range of from about 750° F. to about 860° F. (399°–460° C.). A now preferred temperature for producing methane will be in the approximate range of from about 780° to about 840° F. (416°–450° C.).

Widely varying pressures can be used. Subatmospheric pressure can be used, but is not now preferred. The pressure will ordinarily be in the range of from about atmospheric to about 2,000 pounds per square inch gauge (13.8 MPa). Preferably, however, the pressure will be in the approximate range of from about 50 to about 1,000 pounds per square inch gauge (0.34 to 6.9 MPa).

Varying amounts of catalysts suspended in the molten salt and the overall size of the molten salt bath, as well as its shape, can be determined by mere routine testing. Any suitable catalyst capable in the molten salt of catalyzing the conversion of carbon monoxide and hydrogen to carbon and/or methane can be employed in this process. Finely divided conventionally known methanation catalysts are effective in producing both carbon and methane. For example, finely divided Group VIII metal catalysts are suitable.

The catalyst preferred in the process is finely divided nickel or iron which is suspended in the molten mixture of carbonates. The nickel or iron can be formed in situ by the reduction of nickel oxide or ferric oxide powder dispersed in the melt with the carbon monoxide. Other suitable catalysts include Raney nickel, Raney iron and Raney cobalt or these metals supported on alumina. The powdered Raney metals can be placed into the salt bath in their unactivated form. When Group VIII metal catalysts are employed, the concentration of Group VIII metal is generally from about 0.5 to about 25 weight percent based on the molten salt and the catalyst, preferably from about 1 to about 10 weight percent.

An especially preferred catalyst when significant amounts of methane are desired is a finely divided nickel catalyst. The concentration of nickel metal when the catalyst is active for methanation in the bath will be from about 1 to about 20 weight percent based on total of salt and nickel, preferably from about 1.5 to about 10 weight percent.

The nickel catalyst which can be employed in the molten bath can be selected by mere routine testing. Catalysts included are elemental nickel in powder or wire, e.g., as the element, or in other form and range to combinations of nickel with aluminum, e.g., unactivated Raney nickel, nickel with alumina, etc. A promoter can also be present. Thus calcium aluminate and metal promoters can be present in the alumina. The best catalyst found, thus far, was powdered nickel on alumina containing a minor amount of barium acetate, i.e., about 5 weight percent. Other suitable carriers for the catalyst, when a carrier is employed, can be used.

A particularly effective catalyst in terms of methane production consists of about 20–25 weight percent nickel supported on alumina stregthened with some calcium aluminate. This catalyst is available commercially as Girdler's 65 RS. It is perferably promoted by the addition of about 2.7 weight percent barium added as barium acetate, for example. Nickel in various forms such as powder and wire are effective to a greater or lesser extent when employed as catalysts.

Preliminary experiments showed that the particle size and method of forming were important in obtaining a desirably methanation active catalyst. Nickel particles formed by converting nickel carbonate to the oxide as by calcining in air and reducing the nickel oxide to nickel in situ in the molten alkali melt carbonate bath while passing the synthesis gas therethrough for the methanation reaction were found to have an average particle size of about 1 micron (1 μm) or even smaller, as determined by an optical or a scanning electron microscope. Similarly measured commercially obtained nickel powder had a particle size range of from about 25 to about 40 microns (25 to 40 μm) and showed only slight catalytic activity in the process of the invention.

Thus it now appears that for production of significant amounts of methane the nickel methal catalyst, whether added to or produced in situ in the molten salt, should have a rather small particle size of the order of from less than about 1 to several microns. Presently a particle size of about 1 micron or smaller, employed in the manner and in an amount as herein described, has been found to yield good results.

The most suitable molar ratio of hydrogen to carbon monoxide in the feed for preparing significant amounts of methane will range from about 2.5:1 to about 4.5:1 broadly. Preferably, as will be understood, the stoichiometric ratio of 3:1 is employed for economical reasons.

The feed can be made up by simply mixing suitable proportions of rather pure carbon monoxide and hydrogen. Steam reforming of hydrocarbons, coal, coke, charcoal and the like can be used. Normally it is preferred that other gases, e.g., carbon dioxide, methane, ethane, water and the like be not over 5 volume percent.

Contact times required in the process can vary depending upon the height of the molten carbonate column and the rate of introduction of the feed to the reactor. Generally, the contact times can vary from about 1 second to about 5 minutes. Good results have been obtained at ½–2 minutes total contact times.

While at least some carbon is believed to form whenever the carbon monoxide and hydrogen are reacted in the presence of a methanation catalyst suspended in a molten salt, generally the conditions most suitable for the production of significant amounts of carbon are as follows:

|  | Broad | Preferred |
|---|---|---|
| $H_2:CO$, Mol Ratio | 0.1–3.2 | 0.2–2.5 |
| Bath temperature | 399–800° C. | 416–750° C. |
| Pressure, psig | 0–2000 | 50–1000 |

The feedstock utilized in preparing the carbon is as described above for use in preparing methane, e.g., gases obtained from steam reforming of hydrocarbon, coal, coke, charcoal and the like.

The crude carbon black formed during the process collects on the surface of the carbonate melt. In the runs of the examples of the instant invention it was recovered at the conclusion of the runs. The carbon black is found to contain some of the alkali metal carbonates and possibly some of the catalyst as it collects on the surface of the melt. The recovered black can be purified by washing with water or dilute acid followed by a water wash to remove the entrained material if desired.

Applications for the crude material include its use as a filler in dry cells and as electrodes. The purified material is suitable for use as black pigment, and as reinforcing filler in rubber formulations and the like. In larger scale runs it is envisioned that the carbon black could be recovered intermittently or continuously by suitable collection techniques. An example includes sweeping near or at the surface of the melt with a reciprocating or rotating device to move the carbon black to a collecting vessel adjacent the reaction zone. A jet of hot, inert gas could be similarly used to sweep the surface clean.

The reactor used according to the invention to yield results tabulated herein was of stainless steel and cylindrical in shape with an inlet tube and outlet tube attached thereto to allow passage of the gaseous feedstock and effluent materials. The reactor was contained in an electrically heated furnace, thermostatically controlled, to maintain the desired operating temperature. The temperature of the molten carbonate contained in the reactor was determined by means of a thermocouple in a well located in about the center of the melt. Any other suitable method can be used to heat the reactor and to maintain the required temperature of its contents. Since the methanation reaction is extremely exothermic, heat transfer means would be required to control the heat of reaction in a large scale process if considerable methanation of the carbon monoxide is taking place.

Preliminary experiments show that the stainless steel reactor not containing the eutectic and the stainless steel reactor containing the eutectic carbonate melt are both capable of effecting some methanation of carbon monoxide at the same temperatures and pressures used with the catalysts of the invention. Results indicate that the effect of the reactor alone is trivial compared to the results obtained when a catalyst is suspended in the carbonate melt.

The pressure employed in the reactor was controlled with a back pressure regulator manufactured by Accessory Products Company. The effluent passing from the regulator was cooled to room temperature to separate out liquid water, passed to a gas-liquid chromatography (GLC) analyzer and then to a wet test meter and finally vented to a suitable disposing line. The GLC analyzer operated isothermally with bis($\alpha$-ethoxy-ethyl) adipate and molecular sieve columns. Gases analyzed included carbon monoxide, carbon dioxide, hydrogen, methane, butane, ethane, and propane.

EXAMPLE I

The reactor was charged with 170 g of a mixture consisting of 54.8 g lithium carbonate, 56.7 g sodium carbonate and 58.5 g potassium carbonate. The charge was melted and to it was added 16.21 g of 99.9 percent pure nickel helices made from 10 mil wire which had been previously coiled on a ¼ inch mandrel and then cut into lengths of about ¼ to ½ inch. The carbon monoxide and hydrogen mixture was admitted to the GLC analyzer to be sure the desired ratio was used and then the mixture was routed to the reactor. After flushing out the air the reactor was brought to the desired pressure and the run was started. The conditions used and the results obtained are shown in Table I. Runs were conducted daily for six days for the hours indicated.

Table I

| Hours on Stream | Observations Made | Average Melt Temp., °C. | Average Pressure psig | Feed Rates Hr. | | Mol Ratio | Average Product Analyses, Mole % | | | |
|---|---|---|---|---|---|---|---|---|---|---|
| | | | | CO | $H_2$ | $H_2$/CO | $CH_4$ | $H_2$ | CO | $CO_2$ |
| 0 | — | — | — | 8.6 | 26.3 | 3.0 | — | 76.0 | 24.0 | — |
| 0–6.3 | 10 | 432 | 99 | 8.6 | 26.3 | 3.0 | 9.4 | 70.6 | 13.0 | 6.1 |
| 6.3–13.3 | 13 | 433 | 99 | 8.6 | 27.4 | 3.2 | 11.5 | 70.2 | 7.5 | 8.9 |
| 13.3–20 | 9 | 436 | 100 | 8.65 | 27.60 | 3.2 | 15.7 | 69.3 | 5.4 | 9.4 |
| 20–26.5 | 8 | 436 | 100 | 9.00 | 27.75 | 3.1 | 16.3 | 68.1 | 4.7 | 9.9 |
| 26.5–33.2 | 9 | 435 | 199 | 9.0 | 27.8 | 3.1 | 22.2 | 62.2 | 1.3 | 13.5 |
| 33.2–39.5 | 7 | 433 | 199 | 9.0 | 28.1 | 3.1 | 23.2 | 61.8 | 1.0 | 13.1 |

The results show that conversion started rather slowly but after four days it had increased substantially. The amount of carbon dioxide increased as the test continued. Increasing the pressure from 100 psig to 199 psig appeared to improve the methanation reaction somewhat. The gaseous mixture finally obtained was relatively low in methane and high in hydrogen and some carbon monoxide remained. Such a mixture would not be suitable for heating purposes without additional and extensive purification processes.

EXAMPLE II

A two-step methanation process was carried out in which the effluent gaseous mixture obtained from the molten salt reactor and catalyst employed in Example I was used. The effluent passing from the back pressure regulator of step 1 was passed at atmospheric pressure over 15.8 g of ⅛ inch diameter prills of a nickel on alumina catalyst which contained a small amount of calcium aluminate and additionally promoted with about 5 wt. % barium acetate. A typical catalyst of this type consists of 24 wt. % nickel, 2.7 wt. % barium, 3 wt. % calcium, 27.7 wt. % alumina, the balance being combined oxygen and water. This catalyst was contained in a glass reactor separately heated in a temperature controlled tube furnace. The effluent gas resulting from step 2 was analyzed as before. The conditions used and the results obtained are shown in Table 2. For step 1 the molten salt reactor and catalyst of Example I were used without change.

In the third run an average pressure of 299 psig (2.06 MPa) was used. Carbon black was produced in each run. The crude carbon black was removed from the reactor after the fourth run and washed and dried and found to weigh 3.45 grams.

Analysis of the sample showed the specific surface area by $N_2$, $I_2$, hexadecyltrimethylammonium bromide (CTAB) adsorption measurements, respectively, to be 158 square meters per gram, 185 square meters per gram and 74 square meters per gram. Considerable microporosity and lack of surface oxidation are indicated. Transmission electron micrograph showed the mor-

TABLE 2

| | | Reactor 1 | | | | | Reactor 2 | | | | | | | | |
|---|---|---|---|---|---|---|---|---|---|---|---|---|---|---|---|
| Hours on Stream | Observations in Interval | Melt Temp. °C. | Pressure Psig | Feed Rate, L/Hr | | $H_2$/CO Ratio | Feed Rate L/Hr | Furnace Temp. °C. | Hot Spot* °C. | Average Product Analyses, Mole % | | | | | |
| | | | | CO | $H_2$ | | | | | $CH_4$ | $H_2$ | CO | $CO_2$ | $C_2H_6$ | $C_3H_8$ |
| 0 | — | — | — | 8.7 | 27.6 | 3.2 | — | — | — | — | 73.4 | 26.6 | — | — | — |
| 0.5 | 1 | 435 | 201 | 8.7 | 27.6 | 3.2 | — | — | — | 25.3 | 61.4 | 0.46 | 12.2 | — | — |
| 0.5–6.75 | 8 | 435 | 200 | 8.7 | 27.6 | 3.2 | 9.75 | 287 | 360 | 81.0 | 14.2 | 0 | 4.6 | 0.42 | 0.14 |

*Hot spot refers to the temperature of the catalyst determined by a thermocouple.
The results show that the unsatisfactory gaseous composition resulting from step 1 is favorably resolved by the step 2 process in which the remaining carbon monoxide was entirely methanated. Much of the carbon dioxide apparently reacted with the hydrogen to form methane. As a result of the reactions, the methane content was substantially increased, small amounts of ethane and propane were also produced, the carbon dioxide content was reduced to about its thermodynamic equilibrium concentration and the hydrogen content was substantially reduced as a result of the reactions consuming it. The final gaseous mixture is suitable for heating purposes after the remaining carbon dioxide is removed by following conventional procedures described earlier.
After completing the run, the reactors were cooled down and the solids from reactor 1 were removed and dissolved in water to check the condition of the nickel wire helices. They were found to be intact but covered with some carbon which displayed magnetic properties. The carbon apparently resulted from disproportionation of some of the carbon monoxide. The carbon was separated, washed with water and ignited. Analysis of the ash showed it to contain 24 wt. % iron, 29 wt. % chromium and 6.4 wt % nickel suggesting that the walls of the stainless steel reactor played some part in the formation of the carbon.

EXAMPLE III

The reactor was charged with 170 g of a mixture of the alkali metal carbonates as in Example I which was mixed with nickel oxide powder (21.6 g calculated) obtained by converting 34.4 g of nickel carbonate to the oxide by calcination in air for 1½ hours at 752° F. (400° C.). The nickel oxide was eventually reduced to nickel by the synthesis gas. Examination of nickel produced in this fashion with an optical microscope showed metal phology to be filamentary but highly nonuniform in contrast with the very regular spiral strand structure observed in blacks made from the disproportionation of CO in a highly mobile liquid, e.g., a hydrocarbon over a finely divided solid catalyst. The former black is considered to be superior to the latter for rubber reinforcing.

The nickel/mixed carbonate ratio in the runs was 1 to 10. The conditions used and results obtained are shown in Table III.

TABLE 3

| Hours on Stream | Observations Made | Average Melt Temp. °C. | Average Pressure psig | Feed Rates, L/Hr | | $H_2$/CO Ratio | Average Product Analyses, Mole % | | | |
|---|---|---|---|---|---|---|---|---|---|---|
| | | | | CO | $H_2$ | | $CH_4$ | $H_2$ | CO | $CO_2$ |
| 0 | 0 | — | — | 8.8 | 27.2 | 3.1 | — | 73.3 | 26.7 | — |
| 0–4.5 | 10 | 432 | 148 | 8.8 | 27.2 | 3.1 | 16.7 | 64.5 | 10.2 | 8.3 |
| 4.5–10 | 12 | 430 | 148 | 8.8 | 27.6 | 3.1 | 18.6 | 64.3 | 6.9 | 9.8 |
| 10–11.5 | 2 | 439 | 149 | 8.9 | 27.0 | 3.0 | 20.9 | 62.1 | 6.1 | 10.9 |
| 11.5–16 | 8 | 429 | 299 | 8.9 | 27.0 | 3.0 | 19.4 | 62.8 | 6.3 | 11.3 |
| 16–23 | 8 | 432 | 149 | 9.1 | 27.0 | 2.9 | 20.1 | 63.3 | 5.3 | 11.2 |

The results show that conversion starts somewhat faster than when nickel wire is used but that it still requires about 10–20 hours to effect substantial conversion. The data show after 23 hours compared to 26.5 hours for the nickel wire catalyst of Example I that the nickel oxide catalyst produces more methane but also more carbon dioxide. The amount of carbon dioxide produced is undesirable but it could be reduced, the methane content increased, the hydrogen content decreased and carbon monoxide content completely converted by going to a two step process as in Example II.

particles of about one micron diameter or smaller. The mixture was heated to 500° to assure complete melting and then cooled to about 432° C. before starting the run. A mixture of CO (rate, 8.8 liters/hour) and $H_2$ (rate, 27.2 liters/hour) was passed through the melt. The $H_2$/CO ratio was 3.1. The average temperature of the melt during the run was 429° C. and the average pressure in the reactor was 148 psig (1.02 MPa). The run was terminated after six hours and the reactor cooled to room temperature. Over the next several days, three additional similar runs were made by remelting the charge and again passing the gaseous mixture through the melt. In the runs the melt temperature ranged from about 430° to 431° C. and the pressure ranged from about 148 to 149 psig (1.02–1.03 MPa) in two of them.

EXAMPLE IV(a) and IV(b)

Unactivated Raney nickel powder (50/50 nickel-/aluminum) was used as the catalyst. In part (a), 34 g of Raney nickel (17 g nickel) was suspended in the alkali metal carbonate melt. In part (b), 17 g of Raney nickel (8.5 g nickel) was suspended in the molten carbonate mixture. As in Example I, the reactor was charged with 170 g of the mixed alkali metal carbonates. Daily runs were made in part (a) as in previous Examples. However, in part (b) a continuous run was employed after the first day. Thus, a continuous test was made from 5.5 hours on stream until termination of the run. The conditions employed and the results obtained are shown in Tables 4(a) and 4(b).

which was pulverized into fine powder, consisted essentially of nickel on alumina containing some calcium

TABLE 4

| Hours on Stream | Observations Made | Average Melt Temp. °C. | Average Pressure psig | Feed Rates, L/Hr | | $H_2/CO$ Ratio | Average Product Analyses, Mole % | | | |
|---|---|---|---|---|---|---|---|---|---|---|
| | | | | CO | $H_2$ | | $CH_4$ | $H_2$ | CO | $CO_2$ |
| (a) 34g Raney Nickel Catalyst | | | | | | | | | | |
| 0 | 0 | — | — | 7.6 | 31.9 | 4.2 | — | 78.6 | 21.4 | — |
| 0–6 | 9 | 435 | 148 | 7.6 | 31.9 | 4.2 | 10.1 | 73.7 | 11.2 | 4.6 |
| 6–13 | 12 | 436 | 149 | 7.3 | 32.7 | 4.5 | 20.5 | 69.0 | 3.3 | 7.0 |
| 13–18 | 5 | 430 | 150 | 7.45 | 32.3 | 4.3 | 25.5 | 68.7 | 2.4 | 3.1 |
| 18–25 | 11 | 431 | 148 | 7.5 | 31.1 | 4.1 | 50.8 | 43.5 | 1.7 | 3.5 |
| 25–31.5 | 4 | 437 | 149 | 8.05 | 33.6 | 4.2 | 44.6 | 50.7 | 0.9 | 3.6 |
| 31.5–38 | 11 | 433 | 149 | 7.75 | 32.4 | 4.2 | 48.8 | 48.5 | 0.1 | 2.5 |
| (b) 17g Raney Nickel Catalyst | | | | | | | | | | |
| 0 | 0 | — | — | 7.7 | 32.2 | 4.2 | — | 79.1 | 20.9 | — |
| 0–5.5 | 10 | 425 | 154 | 7.7 | 32.2 | 4.2 | 2.2 | 76.8 | 19.5 | 1.3 |
| 5.5–12.5 | 12 | 428 | 153 | 7.55 | 33.3 | 4.4 | 7.7 | 76.3 | 10.2 | 5.5 |
| 12.5–28 | 10 | 428 | 150 | 7.55 | 33.3 | 4.4 | 15.4 | 73.0 | 4.3 | 6.1 |
| 28–36.5 | 10 | 433 | 150 | 7.55 | 33.3 | 4.4 | 34.0 | 59.1 | 0.4 | 1.9 |

Notes:
Hours on stream from 5.5–36.5 were arbitrarily broken down as shown to follow the course of the reaction. The test ran 1¼ hours longer and terminated due to a plug in the inlet line. No observations were made during this period.

Inspection of the results shown in Tables 4(a) and 4(b) shows that Raney nickel is a much more effective methanation catalyst than nickel alone in either wire or powder form. The quantity of methane produced is substantially higher and the quantity of carbon dioxide is substantially lower when Raney nickel is used. It requires about 24 hours, however, for the Raney nickel catalyst to effect substantial conversion of carbon monoxide from its initial concentration of about 21 mole percent to about 1 mole percent or less. It is also apparent that better and faster results are obtained when the quantity of Raney nickel is about 34 g (17 g nickel or about 9 weight percent of the total Raney nickel-carbonate charge) rather than 17 g (or about 4.5 weight percent of the reactor charge). Both catalysts are excellent methanation catalysts in this process, however.

EXAMPLE V

A continuous run was made in which the carbon monoxide feed rate was 7.3 liters/hour, the hydrogen feed rate was 32.35 liters/hour giving a hydrogen/carbon monoxide ratio of 4.4 and the average pressure was 150 psig (1.03 MPa). The reactor was charged with 170 grams of the alkali metal carbonates as in Example I which was admixed with 17 grams of the same catalyst used in the step 2 reactor of Example II. The catalyst aluminate and promoted with barium acetate. Analysis of the catalyst showed it to be 24 weight percent nickel, 2.7 weight percent barium, 3 weight percent calcium, 27.7 weight percent alumina, the balance being combined oxygen and water. The conditions used and the results obtained are shown in Table 5. During the run, 75 product samples were analyzed. For convenience they have been averaged over 12-hour intervals.

TABLE 5

Nickel On Alumina Catalyst

| Hours on Stream | Observations Made | Average Melt | Temp °C. Melt Surface | Average Product Analyses, Mole % | | | | | | |
|---|---|---|---|---|---|---|---|---|---|---|
| | | | | $CH_4$ | $H_2$ | CO | $CO_2$ | $C_2H_6$ | $C_3H_8$ | $C_4H_{10}$ |
| 0 | 0 | — | — | — | 79.9 | 20.1 | — | — | — | — |
| 2–14 | 12 | 430 | 503 | 32.1 | 62.9 | 1.38 | 3.4 | 0.18 | Trace | Trace |
| 14–26 | 10 | 426 | 471 | 23.5 | 68.4 | 3.1 | 4.6 | 0.28 | 0.05 | 0.05 |
| 26–38 | 9 | 436 | 459 | 27.0 | 66.5 | 2.1 | 3.8 | 0.37 | 0.11 | 0.05 |
| 38–50 | 10 | 473 | 443 | 31.6 | 64.4 | 0.62 | 2.7 | 0.5 | 0.2 | 0.04 |
| 50–62 | 9 | 460 | 436 | 31.8 | 64.9 | 0.27 | 2.0 | 0.6 | 0.3 | 0.06 |
| 62–74 | 10 | 448 | 436 | 32.7 | 64.1 | 0.16 | 2.0 | 0.65 | 0.38 | 0.06 |
| 74–86 | 9 | 436 | 438 | 30.2 | 66.8 | 0.18 | 1.7 | 0.66 | 0.48 | 0.09 |
| 86–94 | 6 | 431 | 449 | 27.0 | 69.0 | 0.30 | 2.1 | 0.9 | 0.57 | 0.14 |

Good methanation was established within two hours with this system and it was nearly complete during the final 60 hours of the run. At equilibrium, no detectable amount of carbon monoxide should remain in the product but since a small amount is present it is apparent that complete contacting with the catalyst has not been accomplished. Increasing the residence time by using a taller column of carbonate melt such as in a larger reactor or introducing the feed into the reactor by a plurality of openings could be helpful in decreasing the amount of carbon monoxide in the effluent. Carbon dioxide yield decreased essentially to equilibrium concentration during the final 60 hours of the test. Methane was the principal product of the reaction with small amounts of ethane, propane, and butane being formed also.

The temperature of the surface of the melt was also recorded during the run. At the start of the run when the average temperature of the melt was close to the reactor temperature the highest temperature observed was 524° C. (975.2° F.) at the surface of the melt. The actual catalysis was occurring at that location. As the run progressed the surface temperature decreased whereas the melt temperature increased. This suggests that the catalysis was moving downward in the melt with the passage of time. Effective heat transfer of the methanation reaction to the melt was taking place. Transfer of the heat to the reactor walls and removal therefrom by conventional techniques such as coolant circulating through a jacket could be effected in larger reactors. Also, the melt can be agitated as with the reacting gases or with an inert gas if this is desired.

The $H_2/CO$ ratio used was about 4 rather than the stoichiometric ratio of 3. Therefore, the product was rich in hydrogen, i.e. about 65-69 mole % average during the latter portion of the run, when excellent methanation was occurring. In a commercial operation, using the stoichiometric ratio of 3, the expected product would be substantially richer in methane and substantially leaner in hydrogen than shown in Table 5.

At the conclusion of the run, which was purposefully terminated by formation of a salt plug, the reactor was cooled. The frozen salt was removed from the reactor in portions for subsequent examination. The portions were removed by hammering on the reactor and do not represent sharp strata of the solidified melt but did provide the information shown in Table 6.

TABLE VI

Analyses of Used Catalyst Fractions

| Sample Weight Grams | Sample Location In Reactor | Metal Concentration, Wt. % | | | |
|---|---|---|---|---|---|
| | | Li | Na | K | Ni |
| 9 | Top | 5.82 | 12.7 | 17.8 | 1.87 |
| 147 | Intermediate | 5.44 | 11.6 | 16.3 | 1.51 |
| 19 | Bottom | 5.42 | 12.6 | 17.2 | 0.16 |

There appeared to be no significant fractionation of the alkali metal carbonates. However, it is seen that the nickel containing catalyst was concentrated in the upper portion of the melt at the termination of the run suggesting that the catalyst was possibly carried upward by the synthesis gas as it traversed upward through the mixed carbonate melt.

EXAMPLE VI

A mixture of 48.1 grams $Li_2CO_3$, 50.1 grams $Na_2CO_3$, 51.8 grams $K_2CO_3$ and 19.5 grams NiO (equivalent to 15.0 grams nickel when reduced by the feed) was charged to reactor and heated to about 442° C. Hydrogen was passed through the resulting melt for 30 minutes at the rate of 19.5 liters/hour to reduce the nickel oxide to nickel while the temperature of the melt was lowered to 417° C. The hydrogen flow was stopped and CO (rate, 19.3 liters/hour) was then passed through the melt. The average temperature of the melt was 414° C. and the average pressure in the reactor was 121 psig (0.834 MPa) during the run which was terminated after 3½ hours. Visual inspection of the cooled melt and reactor indicated very little carbon was formed; hence the process is not effective in converting CO to carbon under the conditions employed. The nickel to molten carbonate ratio was 1 to 10.

EXAMPLE VII

The mixed carbonate charge remaining in the reactor from Example I was remelted and its temperature adjusted to 414° C. A gaseous mixture of $H_2$ (rate, 5.15 liters/hour) and CO (rate, 19.6 liters/hour) was passed through the melt. The $H_2$/CO ratio was 0.26:1. The average temperature of the melt was 416° C. and the average pressure in the reactor was 156 psig (1.08 MPa) during the run which was terminated after 6½ hours. After cooling, the crude black was removed from the reactor by tapping the inverted reactor. The black was purified by washing it with water. The dry product weighed 3.7 grams. The test shows that a mixture of $H_2$ and CO is required for the best production of carbon black.

EXAMPLE VIII

A mixture of 48.1 grams $Li_2CO_3$, 50.1 grams $Na_2CO_3$, 51.8 grams $K_2CO_3$, and 15 grams of 50/50 weight percent unactivated Raney iron was charged to the reactor and melted as before. The iron/mixed carbonate ratio was 1 to 20. A mixture of CO (rate, 20.2 liters/hour) and $H_2$ (rate, 5.2 liters/hour) was passed through the melt. The $H_2$/CO ratio was 0.22. The test was conducted for 24 hours. The average temperature was 421° C. and the average pressure in the reactor was 154 psig (1.06 MPa). At the conclusion of the run 5.7 grams of crude carbon black was removed from the reactor.

EXAMPLE IX

A mixture of 48.1 grams $Li_2CO_3$, 50.1 grams $Na_2CO_3$, 51.8 grams $K_2CO_3$ and 2.1 grams $Fe_2O_3$ (equivalent to 1.5 grams Fe when reduced) was charged to the reactor and melted as before. The iron/mixed carbonate ratio was 1:100. A mixture of CO (rate, 10.65 liters/hour) and $H_2$ (rate, 26.00 liters/hour) was introduced near the bottom of the reactor. The $H_2$/CO ratio was 2.4. The test was conducted for about 24 hours. The average temperature was 425° C. and the average pressure in the reactor was about 150 psig (1.03 MPa). At the conclusion of the run 29.6 grams of crude carbon black was removed from the cooled reactor. It was purified by washing in water, dilute acid and again with water and dried. 14.8 Grams of pure carbon black was obtained which amounts to about 6.8 percent of CO converted to carbon. The specific surface area of the product by CTAB adsorption was found to be 65 square meters per gram.

EXAMPLE X

A run similar to Example IX was conducted except that a different feed ratio was used. In this test CO (rate, 21.0 liters/hour) and $H_2$ (rate, 10.5 liters/hour) was passed through the melt. The $H_2$/CO ratio was 0.5. The test was conducted for about 20 hours, then shut down and the reactor cooled in order to install a new inlet feed tube. The crude carbon black was removed at this time. The carbonate charge was then remelted and the test resumed an additional 4 hours before plugging of the inlet tube again forced the test to be discontinued. At the conclusion of the run the reactor was cooled down and the crude carbon black removed and combined with the product made during the first part of the test. The crude product was purified by washing with water, dilute acid and again with water and dried. The product weighed 31.8 grams, representing a conversion of CO to carbon of about 21 percent. The specific surface area of the purified black by CTAB adsorption was found to be 94 square meters per gram.

Reasonable variation and modification are possible in the scope of the foregoing disclosure and the appended claims to the invention the essence of which is that significant amounts of carbon, methane, or both can be prepared by passing a feedstream of carbon monoxide and hydrogen under suitable conditions through a molten salt bath containing a suitable finely divided catalyst.

That which is claimed is:

1. A process comprising passing a feedstream comprising carbon monoxide and hydrogen into a molten salt bath under suitable reaction conditions, said molten salt bath containing suspended therein a catalytic amount of a finely divided Group VIII metal methanation catalyst, said suitable reaction conditions being such that said carbon monoxide and hydrogen react in said molten salt bath to produce carbon, methane, or both.

2. A process according to claim 1 wherein the molar ratio of hydrogen to carbon monoxide in said feedstream is in the range of about 0.1/1 to about 4.5/1, wherein the pressure is in the range of about 0 to about 2,000 psig, and wherein the concentration of said catalyst is in the range of from about 0.5 to about 25 weight percent based on the weight of the molten salt and said catalyst.

3. A process according to claim 2 wherein said finely divided Group VIII metal methanation catalyst is one or more of the group consisting of nickel, iron, and cobalt catalysts.

4. A process according to claim 3 wherein the size of said Group VIII metal methanation catalyst particles is no greater than 40 micrometers.

5. A process according to claim 4 wherein said molten salt consists essentially of one or more alkali metal carbonate, and wherein the molar ratio of hydrogen to carbon monoxide in said feedstream is in the range of about 0.1/1 to about 3.2/1.

6. A process according to claim 5 wherein the molten salt bath is at a temperature in the range of about 399° C. to about 804° C.

7. A process according to claim 2 wherein the feedstream comprises carbon monoxide and hydrogen and no more than 5 volume percent of other gases.

8. A process for producing carbon, methane, or carbon and methane comprising passing a feedstream comprising carbon monoxide and hydrogen into a molten salt bath having a temperature in the range of about 399° C. to about 804° C., said molten salt containing suspended therein about 0.5 to about 25 weight percent of a finely divided Group VIII metal methanation catalyst based on the weight of said molten salt bath and said catalyst.

9. A process according to claim 8 wherein the molar ratio of hydrogen to carbon monoxide in said feedstream is in the range of about 0.2/1 to about 2.5/1, and the molten salt bath is at a temperature in the range of about 416° C. to about 750° C.

10. A process according to claim 9 wherein said molten salt consists essentially of a ternary eutectic of lithium, sodium, and potassium carbonates, said eutectic having a melting point of about 397° C.

11. A process according to claim 10 wherein said Group VIII metal methanation catalyst consists of nickel particles having an average particle size no greater than about 1 micrometer, said nickel particles being formed in situ in the molten carrier by reducing nickel oxide in the molten carrier with said feedstream.

12. A process according to claim 10 wherein said Group VIII metal methanation catalyst comprises unactivated Raney nickel powder, Raney iron powder, or Raney cobalt powder.

13. A process according to claim 10 wherein said Group VIII metal methanation catalyst comprises a fine powder prepared from a catalyst of nickel supported on alumina.

14. A process according to claim 13 wherein the catalyst of nickel supported on alumina is promoted with calcium aluminate and barium acetate.

15. A process according to claim 14 wherein the catalyst of nickel supported on alumina contains about 20-25 weight percent nickel and about 2.7 weight percent barium.

16. A process according to claim 8 wherein the mole ratio of hydrogen to carbon monoxide in said feedstream is in the range of about 2.5/1 to about 4.5/1, and wherein the molten salt is at a temperature in the range of about 399° C. to about 460° C.

17. A process according to claim 16 wherein said molten salt consists essentially of a ternary eutectic of lithium, sodium, and potassium carbonate, said eutectic having a melting point of about 397° C.

18. A process according to claim 17 wherein said Group VIII metal methanation catalyst consists of nickel particles having an average particle size no greater than about 1 micrometer, said nickel particles being formed in situ in the molten carrier by reducing nickel oxide in the molten carrier with said feedstream.

19. A process according to claim 17 wherein said Group VIII metal methanation catalyst comprises unactivated Raney nickel powder, Raney iron powder, or Raney cobalt powder.

20. A process according to claim 17 wherein said Group VIII metal methanation catalyst comprises a fine powder prepared from a catalyst of nickel supported on alumina.

21. A process according to claim 20 wherein the catalyst of nickel supported on alumina is promoted with calcium aluminate and barium acetate.

22. A process according to claim 21 wherein the catalyst of nickel supported on alumina contains about 20-25 weight percent nickel and about 2.7 weight percent barium.

23. A process comprising passing a feedstream comprising carbon monoxide and hydrogen into a molten salt bath under suitable reaction conditions, said molten salt bath containing suspended therein a catalytic amount of a catalyst in the form of about 10 mil nickel wire helices about ¼ to about ½ inch in length and about ¼ inch in diameter, said suitable reaction conditions being such that said carbon monoxide and hydrogen react in said molten salt bath to produce carbon, methane, or both.

24. A process according to claim 23 wherein the molar ratio of hydrogen to carbon monoxide in said feedstream is in the range of about 0.1/1 to about 4.5/1, wherein the pressure is in the range of about 0 to about 2,000 psig, and wherein the concentration of said catalyst is in the range of from about 0.5 to about 25 weight percent based on the weight of the molten salt and said catalyst.

25. A process according to claim 24 wherein said molten salt consists essentially of one or more alkali metal carbonate, and wherein the molar ratio of hydrogen to carbon monoxide in said feedstream is in the range of about 0.1/1 to about 3.2/1.

26. A process according to claim 25 wherein the molar ratio of hydrogen to carbon monoxide in said feedstream is in the range of about 0.2/1 to about 2.5/1, and the molten salt bath is at a temperature in the range of about 416° C. to about 750° C.

27. A process according to claim 26 wherein said molten salt consists essentially of a ternary eutectic of lithium, sodium, and potassium carbonates, said eutectic having a melting point of about 397° C.

28. A process according to claim 24 wherein said molten salt consists essentially of at least one alkali metal carbonate, wherein the mole ratio of hydrogen to carbon monoxide in said feedstream is in the range of about 2.5/1 to about 4.5/1, and wherein the molten salt is at a temperature in the range of about 399° C. to about 460° C.

29. A process according to claim 28 wherein said molten salt consists essentially of a ternary eutectic of lithium, sodium, and potassium carbonates, said eutectic having a melting point of about 397° C.

* * * * *